US007343305B2

(12) United States Patent
Benn et al.

(10) Patent No.: US 7,343,305 B2
(45) Date of Patent: Mar. 11, 2008

(54) METHOD AND SYSTEM FOR RECORDING CARIOUS LESIONS

(75) Inventors: Douglas K. Benn, Gainesville, FL (US); Stephen H. Kostewicz, Gainesville, FL (US); Douglas D. Dankel, II, Gainesville, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 1153 days.

(21) Appl. No.: 10/136,903

(22) Filed: May 2, 2002

(65) Prior Publication Data

US 2002/0178032 A1 Nov. 28, 2002

Related U.S. Application Data

(60) Provisional application No. 60/288,524, filed on May 3, 2001.

(51) Int. Cl.
  *A61B 5/00* (2006.01)
  *G06F 19/00* (2006.01)
(52) U.S. Cl. .......................................... 705/3; 433/215
(58) Field of Classification Search .................. 433/76, 433/215, 213, 26, 24, 29, 223, 27; 128/898; 600/473, 590, 424, 434; 715/849; 606/12; 707/104.1; 705/2, 3
See application file for complete search history.

(56) References Cited

U.S. PATENT DOCUMENTS 4,869,531 A 9/1989 Rees
5,343,391 A * 8/1994 Mushabac .................... 433/76

(Continued)

FOREIGN PATENT DOCUMENTS

GB 2259162 A 3/1993

OTHER PUBLICATIONS

Paul H. Keyes, "A method of recording and scoring gross carious lesions in the molar teeth of syrian hamsters", Oct. 3, 1944, Carnegie Corporation of New York and the Eastman Dental Dispensary of Rochester, N. Y.*

(Continued)

*Primary Examiner*—Christopher L Gilligan
*Assistant Examiner*—Dilek B. Cobanoglu
(74) *Attorney, Agent, or Firm*—Saliwanchik, Lloyd & Saliwanchik

(57) ABSTRACT

A method and system is provided for charting tooth decay to assist in caries management. Specifically, the invention provides a computer system, a Graphical User Interface (GUI), a method, and associated computer code for presenting an interactive tooth chart comprising selectable, anatomically correct tooth icons corresponding to a dental patient's teeth. The invention allows a user to select regions of each individual tooth icon to record the condition of the selected region. According to the invention, a dental patient is selected from a patient data base, the patent's teeth are examined, and the condition of each tooth region is recorded using selectable icons. The invention further provides automatic characterization of dental conditions based on standard values and previously recorded conditions to indicate progression of disease. In an alternative embodiment, the invention provides a recommended course of clinical management based on the information recorded. In another embodiment the invention automatically classifies patients into risk categories and provides suggested x-ray exam intervals. Thus, particular advantages of the current invention include ease of recording dental conditions, more accurate dental charting, and automatic analysis of recorded dental data, advantageously resulting in better patient care and more efficient use of a dental care provider's time.

50 Claims, 12 Drawing Sheets

U.S. PATENT DOCUMENTS

| | | | |
|---|---|---|---|
| 5,372,502 A * | 12/1994 | Massen et al. | 433/215 |
| 5,554,034 A | 9/1996 | Zand | |
| 5,562,448 A * | 10/1996 | Mushabac | 433/215 |
| 5,636,870 A | 6/1997 | Enhorning | |
| 5,688,118 A * | 11/1997 | Hayka et al. | 433/27 |
| 5,720,502 A | 2/1998 | Cain | |
| 5,738,113 A * | 4/1998 | Connelly | 128/898 |
| 5,823,773 A | 10/1998 | Brysch | |
| 5,944,531 A | 8/1999 | Foley et al. | |
| 5,954,712 A * | 9/1999 | Goodman et al. | 606/12 |
| 5,984,368 A | 11/1999 | Cain | |
| 6,099,314 A * | 8/2000 | Kopelman et al. | 433/213 |
| 6,116,910 A | 9/2000 | Green | |
| 6,162,177 A | 12/2000 | Bab et al. | |
| 6,179,611 B1 * | 1/2001 | Everett et al. | 433/29 |
| 6,206,691 B1 * | 3/2001 | Lehmann et al. | 433/26 |
| 6,227,850 B1 * | 5/2001 | Chishti et al. | 433/24 |
| 6,243,601 B1 * | 6/2001 | Wist | 600/473 |
| 6,402,707 B1 * | 6/2002 | Ernst | 600/590 |
| 6,575,751 B1 * | 6/2003 | Lehmann et al. | 433/223 |
| 6,607,387 B2 * | 8/2003 | Mault | 433/215 |
| 6,648,640 B2 * | 11/2003 | Rubbert et al. | 433/24 |
| 6,664,986 B1 * | 12/2003 | Kopelman et al. | 715/849 |
| 2002/0042039 A1 * | 4/2002 | Kim et al. | 433/29 |
| 2002/0061495 A1 * | 5/2002 | Mault | 433/215 |
| 2002/0193686 A1 * | 12/2002 | Gilboa | 600/424 |
| 2003/0044755 A1 * | 3/2003 | Jensen | 433/215 |
| 2003/0046304 A1 * | 3/2003 | Peskin et al. | 707/104.1 |

OTHER PUBLICATIONS

Ohrn K., Crossner C.-G., Borgesson I., Taube A., "Accuracy of dental hygenists in diagnosing dental decay", 1996, Sweden Community Dentistry and Oral Epidemiology, journal article issue 24/3, pp. 182-186.*

Sharon L. Sheahan, "Documentation of Health Risks and Health Promotion Counseling by Emergency Department Nurse Practitioners and Physicians", Journal of Nursing Scolarship, 32, 2, 245, Fall 2000.*

Speipel s., Wagner I., Koch S., Schneider W., "Three dimensional visulazation of the mandible: A new method for presenting the periodontal status and diseases", Center for human-computer studies, Uppsala University, Lagerhyddvagen, Sweden, 1995, 46/1 (51-57).*

Peterson L. C., Cobb D.S., Reynolds D. C., "ICOHR: Intelligent computer based oral health record", University of Iowa, College of Dentistry, 1995, 8 Pt 2 p. 1709.*

Titus, K. L. et al. "A Portable, GUI-Based, Object-Oriented Client-Server Architecture for Computer-Based Patient Record (CPR) Systems" *Journal of the Society for Health Systems*, 1994, pp. 55-62, vol. 5, No. 1.

* cited by examiner

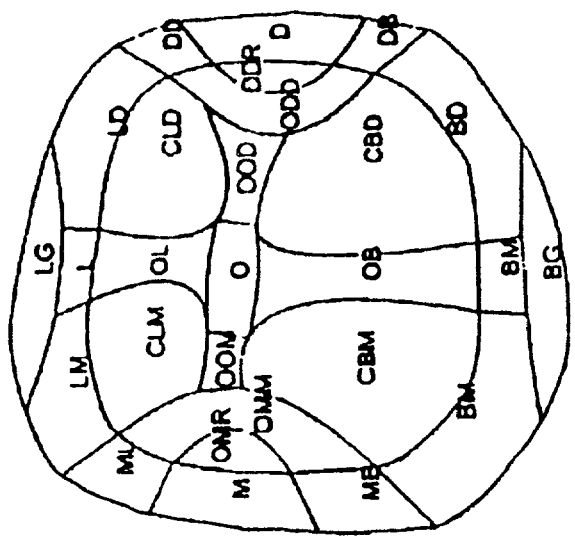
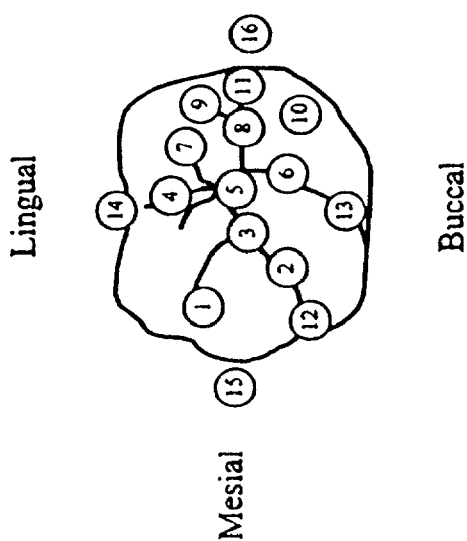
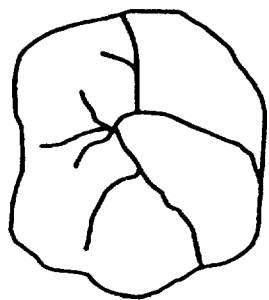
FIG. 2

CLINICAL CARIES CLASSIFICATION

Click on an icon that matches the observed caries.

Sound:
No visible caries

White/Brown Spots on Surface:
- Spot - hard/glossy
- Spot - soft/rough

Non-Cavitated Pits and Fissures:
- Stained hard/glossy pits and fissures
- Stained soft/rough pits and fissures

Non-cavitated Dentin Caries:
- Non-cavitated dentin - hard surface
- Non-cavitated dentin - rough surface

Cavitation:
- Small involving enamel only - hard/glossy
- Small involving enamel only - soft/rough
- Medium involving dentin - hard/glossy
- Medium involving dentin - soft
- Large involving pulp

Root Caries:

Non-cavitated
- Root caries, dentin only - hard
- Root caries, dentin only - soft
- Root caries, involving pulp Cavitated

FIG. 5

RADIOGRAPHIC CLASSIFICATION
Click on an icon that best represents the observed radiographic depth:
 E0 Healthy, no lesion visible (F1)    D1 Lesion in outer third of dentin (F4)
 E1 Lesion in outer half of enamel (F2)    D2 Lesion in middle third of dentin (F5)
 E2 Lesion in inner half of enamel but has not entered dentin (F3)    D3 Lesion in inner third of dentin (F6)
FIG. 6

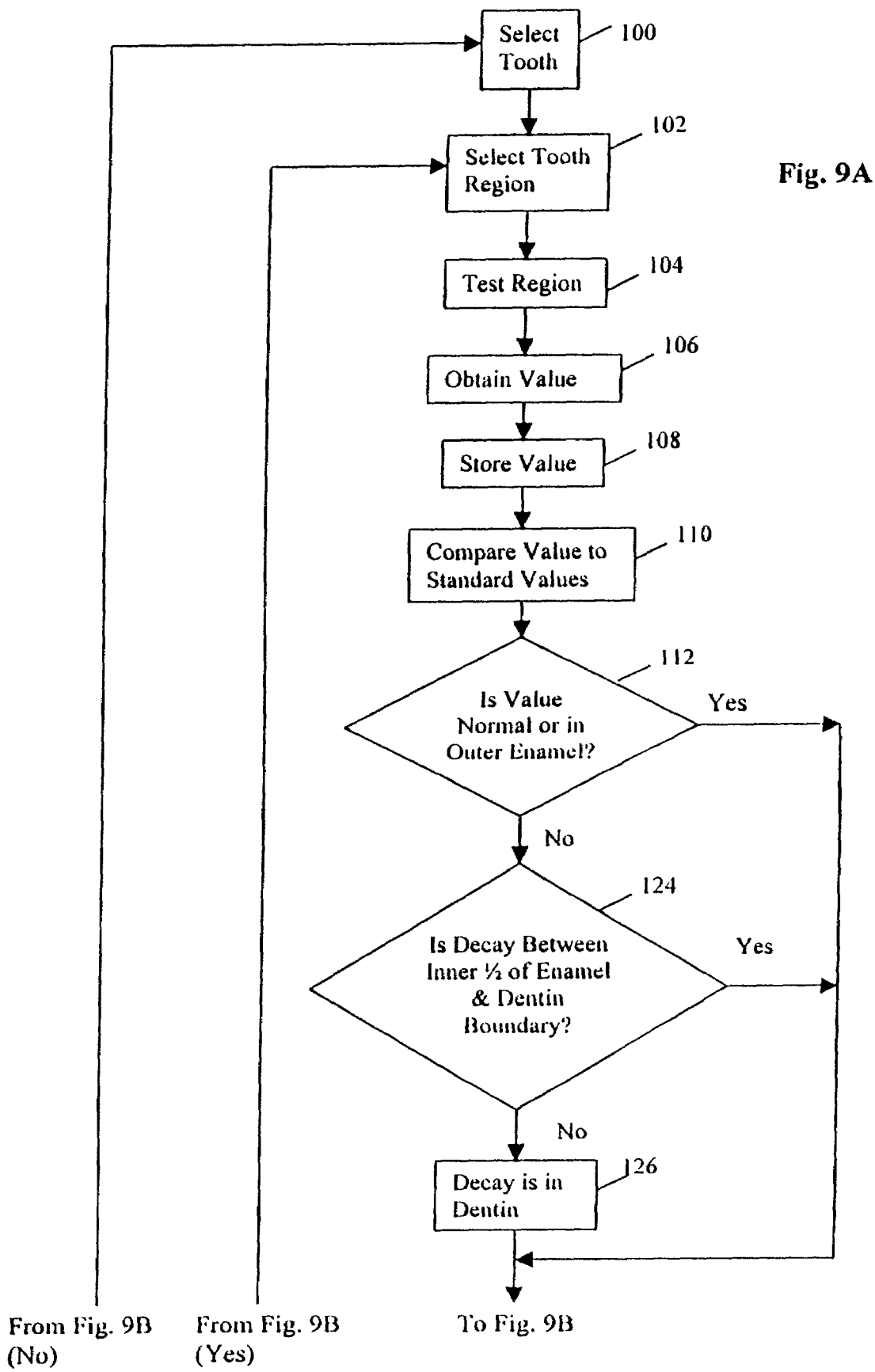

ZERO BASELINE

This patient does not have a recorded zero baseline entry.

A zero baseline entry must be recorded for proper tracking of Diagnodent data.

Please click OK to record the zero baseline tooth and surface.

Today's Appointments

| 08:30 | Joe Patient |
| 09:00 | Jane Doe |
| 11:00 | Sam Jones |
| 11:15 | Arnold Van Breukeler |
| 13:00 | Bobby Taylor |

Name:
Arnold Van Breukeler

Zero Baseline:
  Tooth:
  Surface:

[Back]    (i)

FIG. 10C

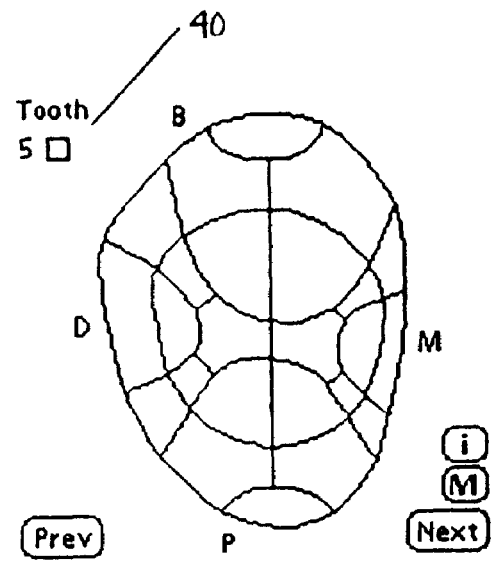

FIG. 10D

METHOD AND SYSTEM FOR RECORDING CARIOUS LESIONS

CROSS-REFERENCE TO A RELATED APPLICATION

This application claims the benefit of U.S. Provisional Application Ser. No. 60/288,524, filed May 3, 2001, incorporated herein by reference.

COPYRIGHT NOTICE

A portion of the disclosure of this patent document, including drawings and screen shots, contains material that is subject to copyright protection. The copyright owner has no objection to the facsimile reproduction by anyone of the patent document or the patent disclosure as it appears in the Patent and Trademark Office patent file or records, but otherwise reserves all copyright rights whatsoever.

TECHNICAL FIELD

The present invention relates to caries management. More specifically, the invention relates to a method and system for charting tooth decay to assist in caries management.

BACKGROUND ART

Individuals seeking dental care often have the records of their examination entered into a chart. The completed chart exhibits the locations of carious, broken and missing teeth. Any work previously performed by a dentist, including restorations, crowns and bridges, is also displayed. Because this information is used for treatment planning, evaluation and patient identification, it must be complete and accurate. Specifically with respect to caries management, existing tooth charts are unable to distinguish between early and advanced tooth decay. As shown in FIG. 1 (PRIOR ART), three different stages of tooth decay are shown in the photographs, but the same chart symbol of a red circle is the conventional way for representing all stages of the disease (manually and electronically). This lack of descriptive detail is a major barrier to modern caries management since the stage and transition from one stage to another is not possible. Moreover, the prior art charting system does not record specific anatomical location and no more than two separate sites on the chewing (coronal) surface.

Accordingly, there is a need in the art for a method and system for advanced caries management which provides more descriptive representations of tooth decay, including site severity, activity (demineralization or remineralizing), and cavitation state (non-cavitated or cavitated) of decay. The cavitation state is extremely important to know since a non-cavitated region of decay can potentially heal itself so that no filling is needed. Dentists who explain to patients that their decay is not cavitated and they clean the area free of bacteria, reduce sugar between meals, and rinse with fluoride are likely to cause the decay to remineralize. No existing tooth decay system records this information.

There is also a need in the art for a simple graphical user interface (GUI) to make entering and viewing data relative to caries management easier. It is well known that the development and proliferation of GUIs have greatly enhanced the ease with which users interact with data both in the entry and in the display of information. A conventional GUI display includes a desktop metaphor upon which one or more icons, application windows, or other graphical objects are displayed. Typically, a user interacts with a GUI display utilizing a graphical pointer, which the user controls with a graphical pointing device, such as a mouse, touch pen, trackball, or joystick. For example, depending upon the actions allowed by the active application or operating system software, the user can select icons or other graphical objects within the GUI display by positioning the graphical pointer over the graphical object and depressing a button associated with the graphical pointing device. In addition, the user can typically relocate icons, application windows, and other graphical objects on the desktop utilizing the well known drag-and-drop techniques. By manipulating the graphical objects within the GUI display, the user can control the underlying hardware devices and software objects represented by the graphical objects in a graphical and intuitive manner.

A number of patents exist which relate to patient charting and/or caries management, including, U.S. Pat. No. 4,869,531 to Rees, U.S. Pat. No. 5,554,034 to Zand, U.S. Pat. No. 5,636,870 to Enhorning, U.S. Pat. No. 5,720,502 to Cain, U.S. Pat. No. 5,823,773 to Brysch, U.S. Pat. No. 5,944,531 to Foley, U.S. Pat. No. 5,984,368 to Cain, U.S. Pat. No. 6,116,910 to Green, and U.S. Pat. No. 6,162,177 to Bab et al., all of which are incorporated by reference herein.

DISCLOSURE OF THE INVENTION

Broadly speaking, the present invention relates to caries management. More specifically, the invention relates to a method and system for charting tooth decay to assist in caries management.

The invention can be implemented in numerous ways, including as a system (including a computer processing or database system), a method (including a computerized method), an apparatus, a computer readable medium, a computer program product, or a data structure tangibly fixed in a computer readable memory. Several embodiments of the invention are discussed below. A paper-based version of the invention could be used to record the data manually using an enlarged version of the computer screen representation. It would be possible to record the anatomical location, severity, and activity of a carious lesion but the time involved to record the data could make the task impractical and would not have the computer advantages or automatic comparison of changes over time.

As a computer system, an embodiment of the invention includes a memory unit containing data, a display, and a processor unit. The system may be, for example, in the form of a desktop, laptop, handheld, or palm-sized device, or a personal data assistant (PDA), or integrated with other devices. The display has at least one display area (window). The processor unit operates to receive input from the user (keyboard, mouse, pen, voice, touch screen, or any other means by which a human can input data into a computer, including through other programs such as application programs or devices such as a probe), store the input as data, and output the data to the screen or printer. The data may also be transmitted to another device, such as a computer, or transferred via electronic means (including Internet communications). The memory unit may store the protocol for the method of recording carious lesions. The display device may include icons representative of the method of the present invention. The computer system further includes a graphical user interface (GUI) for the display screen for searching, inputting, and displaying data. A variety of formats for searching, inputting, and displaying data is provided.

In a specific example, a graphical representation of all of the teeth of a patient is displayed on a device (preferably hand-held) from which a specific tooth is selected. That tooth is then displayed with individual anatomical graphical regions delineated. The region on the display that corresponds to the region on the actual tooth being examined is selected (or the regions can be automatically activated in a predetermined order). If using a digital probe, the reading on the probe is recorded (directly or manually) for the selected region on the screen. If manual probing is conducted, the operator enters the appropriate data for that region. Voice recognition and voice output may be used in conjunction with the method. Readings are recorded for each region as necessary. The process is repeated for each tooth as necessary. A printout of the chart can then be provided from the device or from a central system with which the device communicates (e.g., PDA synchronized with desktop).

An embodiment of the invention further includes the operations generating caries risk assessment categories for patients.

Another embodiment of the invention includes the operations of recording severity, cavitation state and activity of decay at individual tooth sites for caries management. Color coding may be utilized to differentiate readings or progression. A unique layout of regions for systematic examination is also provided (FIG. 2, e.g., regions 1-16).

As a computer readable media containing program instructions, an embodiment of the invention includes: computer readable code devices for the specific operations of the invention, including graphical display of the teeth, unique display of regions for systematic examination, input of data (manually or directly from another instrument), recording of data, display of data, and output of data. The methods of the present invention may be implemented as a computer program product with a computer-readable medium having code thereon. The program product includes a program and a signal bearing media bearing the program.

As an apparatus, the present invention may include at least one processor, a memory coupled to the processor, and a program residing in the memory which implements the methods of the present invention.

Therefore, it is an object of the present invention to provide a unique system for caries management which allows more detailed information to be recorded.

It is another object of this invention to provide a hand-held-type computer system to allow users to quickly and accurately record the condition of a patient's teeth.

It is still another object of this invention to provide linked interactive display screen that allows a user to select an individual tooth and tooth regions from a diagram of a set of teeth to record the condition of the tooth regions.

It is yet another object of this invention to provide an interactive, detailed tooth representation comprising interactive regions, uniquely identified and corresponding to the coronal morphology of the represented tooth.

It is still yet another object of this invention to provide a caries detection dental probe operated in conjunction with the system to provide a decay value reading for input into the system.

It is another object of this invention to provide a characterization of tooth condition based on current tooth condition and past recorded tooth condition.

It is yet another object of this invention to provide a system for surveying the recorded tooth condition data to recommend clinical management of the condition.

It is still yet another object of this invention to provide a system for generating caries risk assessment categories for patients.

The advantages of the invention are numerous. One significant advantage of the invention is that it allows the user to record the location, severity, activity and cavitation state of decay. In particular, using a caries detection dental probe, tooth condition can be recorded in an efficient and reliable manner. As a result, better caries management can be obtained. The dentist is able to more efficiently and effectively chart the condition of a patient's teeth than conventionally possible. In addition, diagnosis can be automated based on standard caries conditions and previously recorded caries conditions. Furthermore, clinical management decision can be automatically suggested based on tooth condition data.

Other aspects and advantages of the invention will become apparent from the following detailed description taken in conjunction with the accompanying drawings, illustrating, by way of example, the principles of the invention.

All patents, patent applications, provisional applications, and publications referred to or cited herein, or from which a claim for benefit of priority has been made, are incorporated herein by reference in their entirety to the extent they are not inconsistent with the explicit teachings of this specification.

BRIEF DESCRIPTION OF THE DRAWINGS

In order that the manner in which the above-recited and other advantages and objects of the invention are obtained, a more particular description of the invention briefly described above will be rendered by reference to specific embodiments thereof which are illustrated in the appended drawings. Understanding that these drawings depict only typical embodiments of the invention and are not therefore to be considered to be limiting of its scope, the invention will be described and explained with additional specificity and detail through the use of the accompanying drawings in which:

FIG. 2 shows a numerical system for locating anatomical regions of the present invention.

FIG. 5 shows an example of the graphical icons of the present invention used to classify caries.

FIG. 6 shows an example of the graphical icons of the present invention used to classify radiographic depth.

FIG. 9A shows a flow chart for operation of the invention.

FIG. 10A shows an exemplary screen display for indicating daily appointments for dental patients.

FIG. 10B shows an exemplary initial screen display for establishing a zero baseline for a dental patient.

FIG. 10C shows an exemplary tooth chart screen display for establishing a zero baseline for a dental patient.

FIG. 10D shows an exemplary screen display for an individual tooth icon having selectable tooth regions for establishing a zero baseline.

Figure 1:
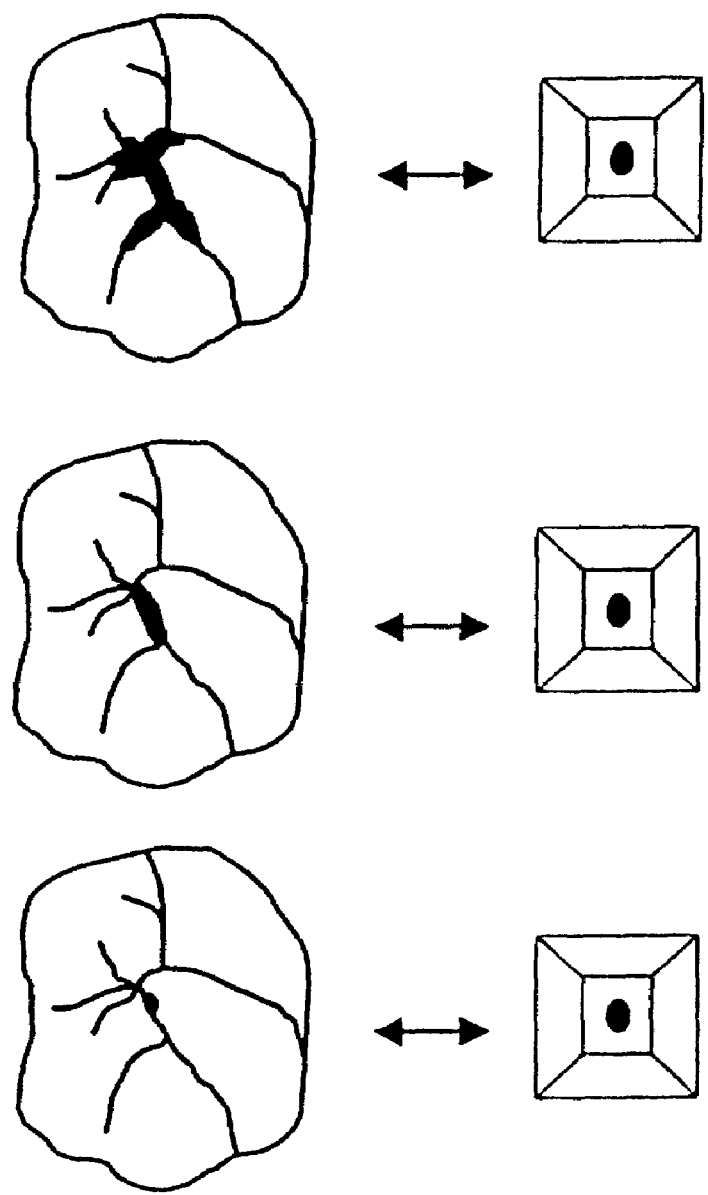
FIG. 1 illustrates different lesions on a tooth's surface with the corresponding conventional chart diagram for caries representation of the prior art.

It should be understood that in certain situations for reasons of computational efficiency or ease of maintenance, the ordering and relationships of the blocks of the illustrated object and functional block diagrams could be rearranged or re-associated by one skilled in the art. The ordering and content of the exemplary display screens may also be rearranged. While the present invention will be described with reference to the details of the embodiments of the invention shown in the drawings, these details are not intended to limit the scope of the invention.

DETAILED DESCRIPTION OF THE PREFERRED EMBODIMENT

Referring now to the drawings, the preferred embodiment of the present invention will be described.

In order to address the problems in the art, the present invention includes a unique recording method as shown in FIG. 2, wherein regions are assigned to the corresponding coronal morphology of the represented tooth. The tooth depicted at the left shows the complexity of the pit and fissure patterns of a common human tooth. A convenient system for identifying each unique coronal morphology area is notably lacking in the prior art. In the middle of FIG. 2, one embodiment of a numerical system for locating anatomical regions is shown. In this example, numbers 1 to 11 show occlusal pits and fissures, while 12, 13, and 14 show buccal and lingual fissures. The number ordering preferably goes from the most mesio-lingual point of the occlusal surface to the most disto-buccal. In order of priority, the numbers are occlusal surface, buccal, lingual, mesial and distal surfaces.

Moreover, in an embodiment of the invention, the regions may be colored (or visually distinguished in another manner) so that, for example a "green 6" would indicate region 6 was re-mineralizing (repairing) while a "red 8" would be demineralizing (getting deeper). In a preferred embodiment, preformed templates, defining specific regions and identified by unique numbers, are provided to guide the user on how to enter data for the selected regions. Alternatively, a user can customize the regions of a selected tooth by adding extra regions or moving regions around if desired (customization).

In an embodiment shown to the right in FIG. 2, a region designation scheme corresponding to compass directions and defined by representative lines delineating individual regions is depicted. Advantageously, techniques for identifying fine directions on a compass rose are applied to region locations. The four cardinal directions, North (N), East (E), South(S) and West (W) can be combined to describe directions between them. For example, N and E can be combined to indicate a direction exactly halfway between N and E or NE. Further, a direction exactly halfway between N and NE can be defined as NNE.

Similarly, as shown in the right hand side of FIG. 2, this technique can be applied to regions of a tooth where the corresponding cardinal directions are Lingual (G) corresponding to N, Distal (D) corresponding to E, Buccal (B) corresponding to S, and Mesial (M) corresponding to W. In addition, Gingival (G), Palatal (P), Cusp (C), Occlusal-Distal Ridge (ODR) and Occlusal-Mesial Ridge (OMR) areas are defined. The center region of the tooth is further defined as Occlusal (O) and, moving out from this center, specific regions are defined in a manner similar to the compass technique. For example, moving from O towards the L side of the tooth, the regions are consecutively identified as OL, L, and, finally, LG to identify to outermost lingual region adjacent to the gum. The regions defined according to the described numbering scheme are shown the exemplary tooth icon on the right hand side of FIG. 2.

I. Interactive Tooth Chart

Figure 3:
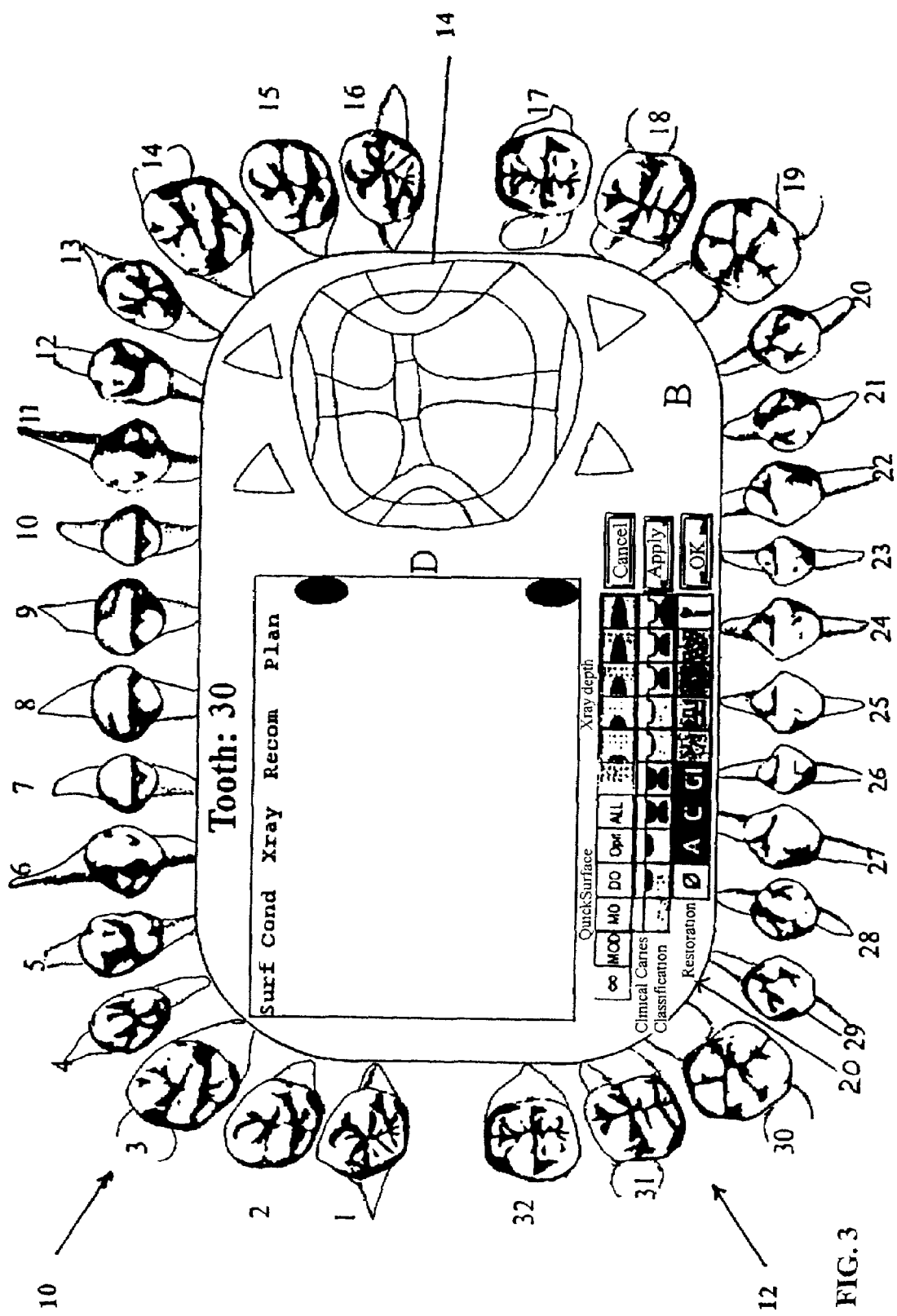
FIG. 3 shows one example of a typical screen display of the present invention showing a specific tooth selected and the icons for entering caries classification and other data.
Figure 7:
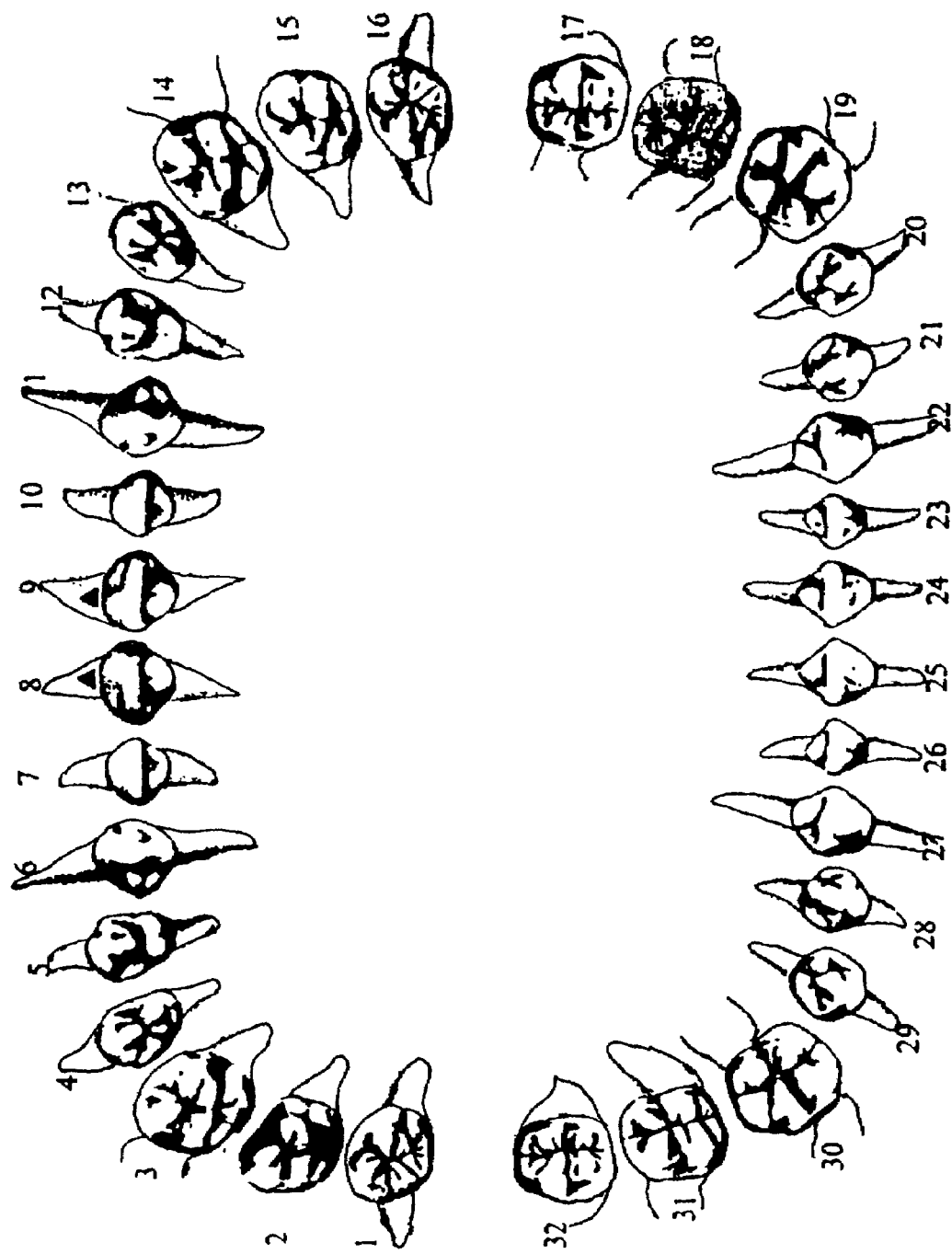
FIG. 7 shows an example of a typical screen display of the present invention showing a set of teeth for a specific patient with carious regions indicated (severity and location).

FIG. 3 shows one example of a typical screen display of the present invention showing a specific tooth (tooth display) 14 selected, and the diagnostic icons 20 for entering caries classification and other data. The diagnostic icons 20 are more specifically illustrated in FIGS. 5 and 6. In the depicted embodiment of FIG. 3, a tooth chart diagram, representative of a set of human teeth, is provided around the periphery of the display area. The diagram is arranged to correspond to tooth placement in a patient's mouth, from the perspective of a user examining the patient's teeth. Accordingly, the top half 10 of the display represents the corresponding tooth arrangement in a patient's upper jaw, and the lower half 12 of the display represents the corresponding tooth arrangement in a patient's lower jaw. In addition, each tooth is numbered according to standard dental charting. The tooth chart shown herein uses anatomically accurate representations of coronal morphology that allows recording of multiple separate lesions on any one tooth. Additionally, the buccal, lingual, mesial, distal, and root surfaces are visible with up to 34 discrete surface tooth surface regions available for recording caries data. In an embodiment, each displayed tooth represents the condition of the patient's teeth as recorded in a patient database of patient dental records. For example, each tooth indicates the presence of caries, fillings, crowns, bridges or other dental work or disease associated with the individual tooth. FIG. 7 shows an example of a typical screen display of the present invention showing a set of teeth for a specific patient with multiple carious lesions indicated (severity and location), as well as fillings.

Each of the teeth in the tooth chart of FIG. 3 is an icon that is linked to an enlarged tooth display 14, depicted when a user selects an individual tooth from the diagram. The enlarged tooth display 14, is further divided into regions corresponding to the coronal morphology and roots of the selected tooth. For example, seven separate occlusal fissure and four occlusal cuspal regions are identified for a lower molar depicted in the enlarged tooth display 14. Such detail assists the user in pit and fissure lesion monitoring. Preferably, the number of pit and fissure regions is 15 or more plus the individual site labels that are necessary to prevent confusion in identifying sites.

According to the invention, each region is an interactive icon that a user selects to record the condition of the selected region. In an alternative embodiment, a region customizer tool is provided to allow a user to customize the regions by interactively adding, altering, or moving regions. In an additional embodiment, a user can graphically capture an image of the coronal morphology of a patient's tooth to create a custom tooth display. For example, a user can employ an intra-oral camera to acquire an image of a patient's tooth and import the image into the patient information database. Once the image is imported, a user can retrieve the image as an interactive tooth icon. Using the newly created tooth icon, a user can assign interactive regions by using the region customizer tool. Subsequently, the newly created icon with the associated interactive regions is automatically displayed whenever the associated patient's dental records are retrieved.

II. Diagnostic Recording

Using the region icons on the enlarged tooth display 14, a user selects a tooth region to be examined, and then examines the corresponding region on the patient's tooth. Diagnosis can be provided by visual inspection, mechanical inspection, x-ray inspection, or other techniques used in the art. In an embodiment, a caries detection dental probe is used to provide a diagnostic indication of caries by applying the probe to selected regions of the patient's teeth. In addition, the caries detection dental probe can be operably connected to the invention so that the diagnostic indications provided by the probe are automatically recorded.

Figure 4:
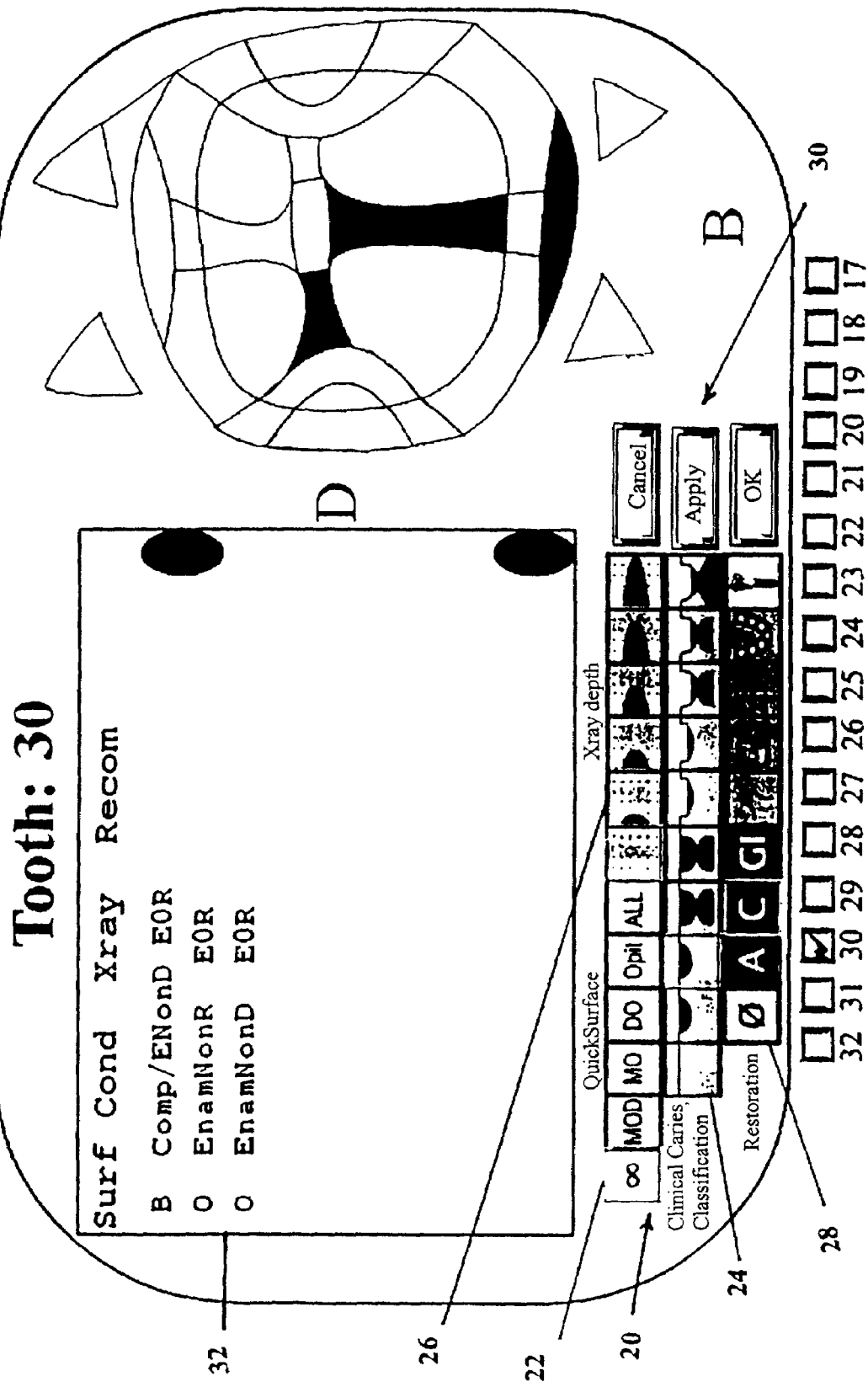
FIG. 4 shows another example of a typical screen display of the present invention showing a specific tooth selected, regions with data entered, additional textual data, and the icons for entering caries classification and other data.

As shown in FIG. 4, rows of diagnostic icons 20 are provided to allow for rapid entry of data regarding the condition of the selected region. For example, the diagnostic icons 20 include common surface combinations, clinical and radiographic appearance of lesions, and a choice of restoration materials, crowns, bridges, dentures, and implants. In an embodiment, the diagnostic icons are grouped into quick surface 22, clinical caries classification 24, x-ray depth 26, and restoration 28 categories. These categories are more specifically described in FIGS. 5 and 6. Selection of multiple icons allows combinations of clinical and x-ray appearance of carious lesions plus existing restoration/recurrent caries information to be easily applied to a tooth region by clicking on the associated region of the enlarged tooth display 14 and selecting the appropriate diagnostic icon. In addition, control icons 30 are provided to allow a user to apply a selected diagnostic icon to a region, cancel the application of a diagnostic icon, and complete diagnostic icon entering for the current region by selecting "OK." In an embodiment, an indication, such as shading of the region or a dot icon in the region, is provided when a diagnostic condition has been applied to the region, thereby notifying the user that the region has been assessed.

A typical example of a recorded diagnosis for several tooth regions is depicted in FIG. 4. In FIG. 4, a buccal composite with early non-cavitated demineralizing recurrent caries, but no radiolucency is shown. Also shown is an occlusal enamel-only, non-cavitated, demineralizing lesion with no radiolucency, and a separate occlusal enamel-only, non-cavitated, demineralizing lesion with no radiolucency.

As shown in FIG. 4, a diagnostic display area 32, is also provided to indicate the recorded diagnosis and recommendation for each region of the selected tooth examined. In an embodiment, the display provides a column for displaying an identifier for each region examined, a column for displaying the recorded condition of the associated region selected, a column for displaying the x-ray results, and a column for displaying the recommended action. The display is scrollable to allow a user to view all recorded information.

III. Treatment Assessment

According to another embodiment of the invention, the diagnostic information as recorded above can be further processed to provide additional information. Specifically, the recorded information can be compared to accepted standard dental values, such as standard values corresponding to extent of caries, to characterize each region examined. By comparing against a standard, a region can be characterized to allow a user to determine the need for treatment. For example, if the comparison shows that the caries is within normal value ranges, no treatment may be necessary. Conversely, if the comparison reveals that the caries is between the inner one half of the enamel and dentin boundary, or in the dentin, treatment may be indicated.

Furthermore, the recorded diagnostic information may be operated on to compare the current condition value of a region to a previously recorded condition value to indicate the progression of caries for the selected region. For example, if the current condition value is more, or worse, than the associated previously recorded condition value, then an indication, such as a red colored indicator, can be provided on the associated region icon to indicate demineralization. On the other hand, if the current condition value is less, or better, than or the same as the previously recorded condition, then an indication, such as a green colored indicator, can be provided on the associated region icon to indicate remineralization or no change, respectively.

IV. Risk Assessment

According to another embodiment of the invention, patient screening information, in conjunction with diagnostic information gathered using the invention, is used to automatically classify patients into low, medium, or high risk categories for developing caries. According to an embodiment, patients are automatically assessed for caries risk based on initial screening information input via a keyboard or other data entry method and caries data entered into the tooth chart by a dentist or an auxiliary. Caries risk screening factors are automatically identified from the screening information and are given numerical values. In an embodiment, screening information is input into the system in according to the answers a patient provides in response to screening questions. For example, screening questions can include questions regarding frequency of brushing and flossing, snacking frequency between meals, sugar use, fluoride use, smoking and alcohol use. Caries risk screening factors are automatically computed and assigned based on the screening information.

Caries risk charting factors are automatically assigned based on tooth charting data and are given numerical values. In an embodiment, enamel lesions are assigned lower numbers than dentin lesions. The risk numbers are automatically added, thresholds applied, and risk level generated. For example, a dentin lesion will automatically generate a medium-risk level classification. If other factors are present in either the screening data or tooth chart (such as enamel lesions), the numerical values corresponding to the other factors are added, so that, for example, a patient who is low risk with two minor risk factors may become high risk when a dentin lesion is added.

The risk classification directly affects the decay management for a patient. Decay management falls into three categories: 1) monitoring a lesion; 2) fissure sealing a lesion; and 3) placing a filling. When a lesion is recorded in the tooth chart, the invention automatically examines the lesion severity, activity, cavitation state, and caries risk level before making a treatment recommendation. For example, for a low-risk patient with a non-cavitated clinical caries in enamel which is remineralizing with no radiolucency, the invention will automatically generate a "monitor" recommendation. For medium- or high-risk patient with a non-cavitated clinical caries in enamel which is remineralizing with no radiolucency, the invention will automatically generate a "fissure seal" recommendation. Further, for a low-risk patient with a non-cavitated clinical caries in enamel that is remineralizing with a dentin radiolucency, the invention will automatically generate a "restore" recommendation and the risk will change to medium or high depending on the numerical score for the pre-existing low-risk number.

The risk model automatically takes into account that caries is a multi-factorial disease and thereby exhibits a high negative predictive value (typically 80-90%). Advantageously, the invention can accurately predict which patients will not develop caries.

In an embodiment, the current invention recommends low caries risk patients are examined at extended intervals of 12 months. The invention compensates for a false positive high caries risk classification, by reducing the high risk classification to medium risk if the patient does not develop a carious lesion within a fixed interval. After a further interval with no caries lesions, the patient will be reduced to a low risk classification. Notably, high risk patients are examined at 3-month intervals. However, if at 12 months, a high risk patient has not developed new carious lesions or progression of existing lesions, the risk level will be automatically reduced to medium risk, and a 6 month re-exam interval will be recommended. If after a further 12 months, no caries has developed, the risk level is further reduced to low and an annual re-exam interval is suggested.

Figure 8:
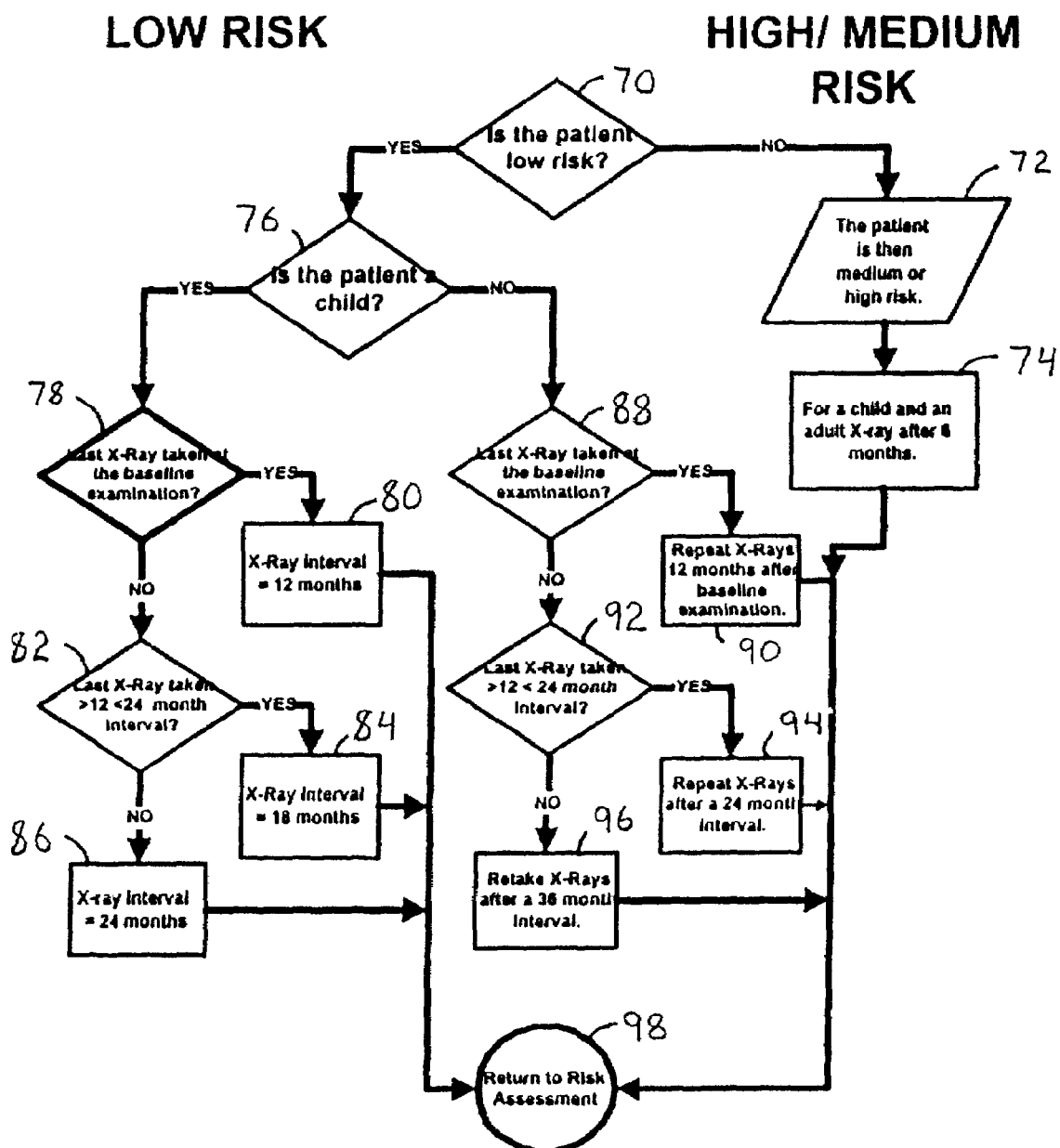
FIG. 8 shows a flow chart for determining radiographic examination intervals.

In addition to recommending exam intervals, the invention also provides x-ray exam recommendations regarding frequency of exposures. Once the risk level for a patient is determined as described above, the appropriate radiographic examination period is automatically determined from caries risk level, age, and time interval since the last recorded x-ray exams. Based on these factors, x-ray exams are suggested at increasing intervals from one to three years. The flow chart of FIG. 8 shows how the invention determines the appropriate x-ray interval.

Initially, a determination is made whether the patient is in a low risk 70 or in a medium/high risk category 72. If the patient is medium or high risk, the system recommends a 6 month x-ray exam period 74 and returns to risk assessment 98. If the patient is low risk, the system then determines if the patient is a child 76. If the patient is a child, the system determines if the last x-ray was taken at a baseline examination 78. If the last x-ray was taken at a baseline examination, the system recommends a 12 month x-ray exam period 74 and returns to risk assessment 98. Alternatively, if no x-ray was taken at a baseline examination, the system determines if the last x-ray was taken between a 12 to 24 month period 82. If the last x-ray was taken between a 12 to 24 month period, an x-ray interval of 18 months is selected 84, and processing continues with a return to risk assessment 98. Alternatively, if the last x-ray was not taken between a 12 to 24 month period, the system recommends a 12 month x-ray exam period 86 and returns to risk assessment 98.

If the patient is not a child in step 76, the system determines if the last x-ray was taken at a baseline examination 88. If an x-ray was taken at a baseline examination, the system recommends a 12 month x-ray exam period 90, and returns to risk assessment 98. On the other hand, if no x-ray was taken at a baseline examination, the system determines if the last x-ray was taken between a 12 to 24 month period 92. If the last x-ray was taken between a 12 to 24 month period, an x-ray interval of 24 months is selected 94 and processing continues with a return to risk assessment 98. Alternatively, if the last x-ray was not taken between a 12 to 24 month period, the system recommends a 36 month x-ray exam period 96 and returns to risk assessment 98.

V. Operation

An example of the use of the present invention will now be described with reference to the steps illustrated in the flow charts of FIGS. 9A and 9B, and the screen shots of FIGS. 10A-10H. Initially the dentist (or other user) selects a patient from the patient database. In the embodiment shown in FIG. 10A, patients are displayed according to appointment schedules for the current day. If the selected patient is a new patient, the zero baseline screen is shown in FIG. 10B. Zero baseline information is then recorded for each tooth and this information stored for later use and comparison to subsequent exam information to track tooth condition. If a baseline has already been recorded for a patient, the zero baseline screen is bypassed and the tooth chart screen, comprising a graphical representation of the patient's teeth, is displayed as shown in FIG. 10C. From the numbered teeth, a user can select an individual tooth for exam. Notably, a back icon ("Back") and an information icon ("i") are provided on the screen display to return to the previous screen or pull up an information menu, respectively. Once an individual tooth has been selected, the corresponding tooth icon having selectable regions is displayed as in FIG. 10D. The display provides and indication of the current tooth selected 40, "Prev" and "Next" icons to navigate among screens, an "i" icon, and a mouth ("m") icon to return to the tooth chart screen. Upon returning to the tooth chart screen of FIG. E from an individually selected tooth screen, the selected tooth 42 and tooth surface 43 are indicated, and an edit icon 44 is provided, to allow editing of the information entered.

Figure 9B:
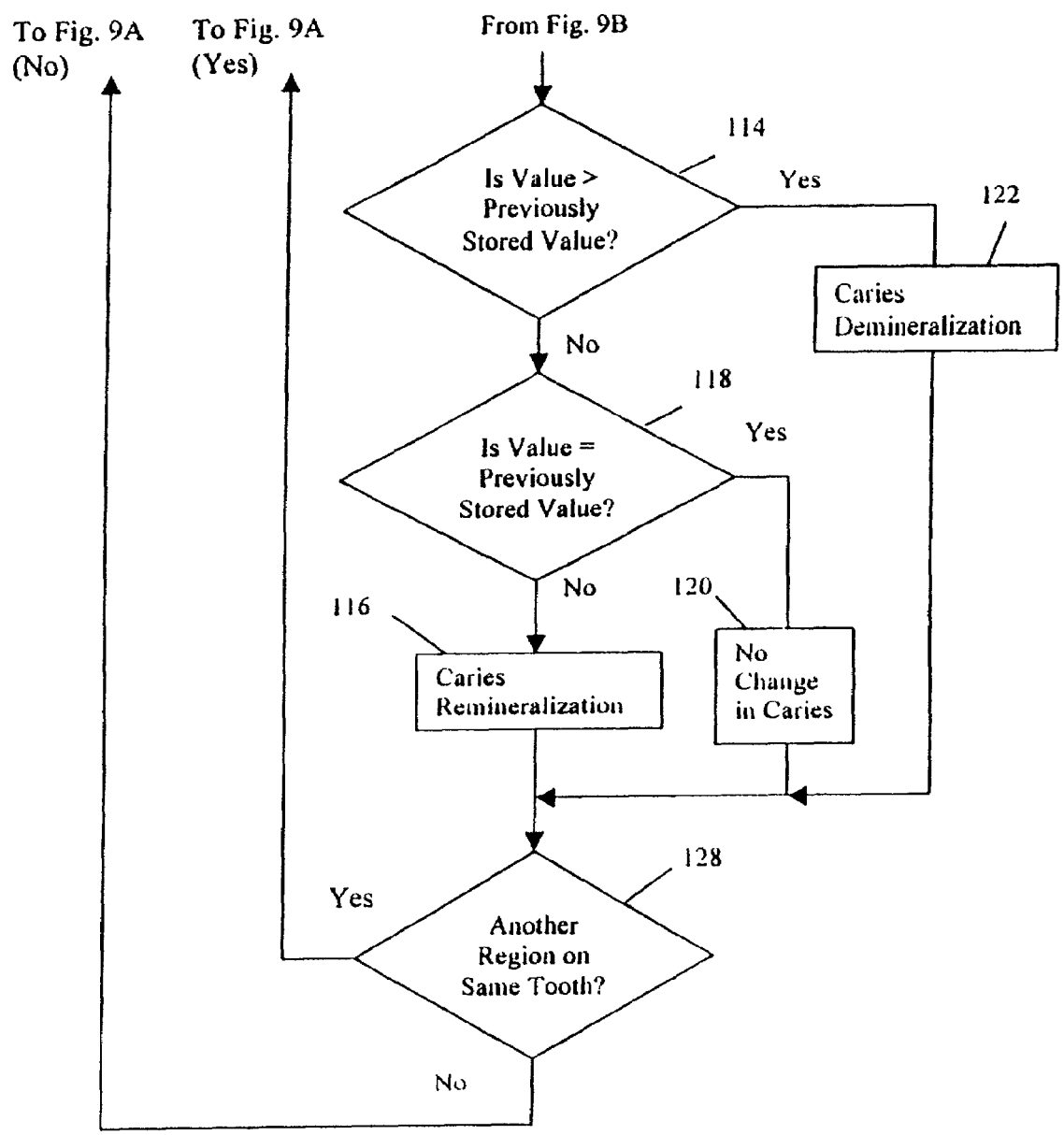
FIG. 9B shows a continuation of the flow chart for operation of the invention.
Figure 10E:
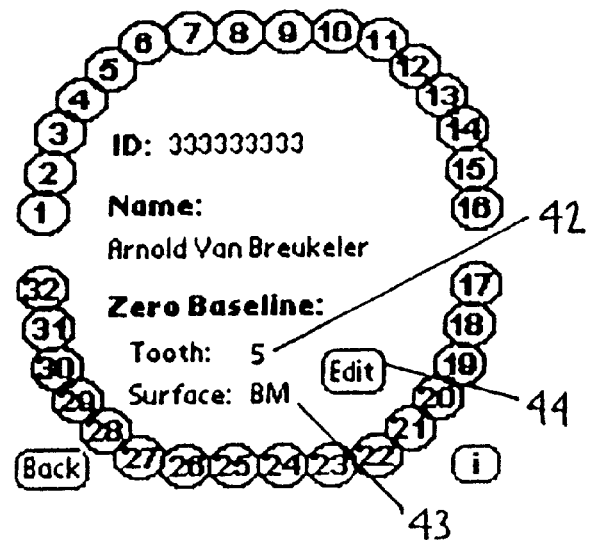
FIG. 10E shows an exemplary tooth chart screen display having indicia for a currently selected tooth.
Figure 10F:
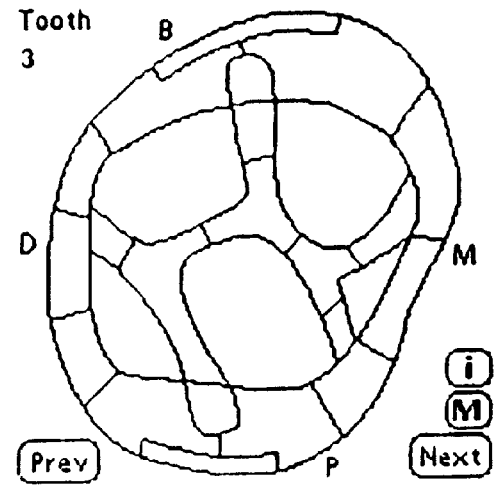
FIG. 10F shows an exemplary screen display for an individual tooth icon having selectable tooth regions for recording the condition of a patient's tooth.
Figure 10G:
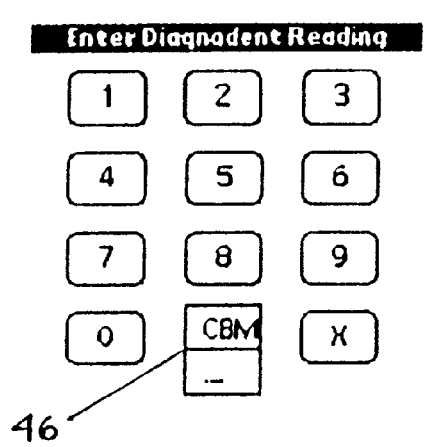
FIG. 10G shows an exemplary numeric keypad screen display for inputting diagnostic values.

Turning now to the flow charts of FIGS. 9A and 9B, a user selects an individual tooth 100 from the graphical representation of the patient's teeth on the display. Then the user selects a specific site (region) on the tooth 102 which the user will be examining. (See FIG. 10F). For convenience, the invention provides a predetermined number of selectable regions for each tooth surface. However, additional numbered sites can be provided by graphically pasting extra sites on top of the existing tooth graphic or capturing an image of a tooth using an inta-oral camera and sites can be graphically pasted by the operator onto the image. Once a region is selected, a numeric keypad screen is automatically displayed as depicted in FIG. G. Notably, the keypad includes a current region indication 46 to display the current region identifier and a value associated with the condition of that region.

The user then applies diagnostic tests 104 to the actual tooth's surface, as known in the art. For example, KaVo America Corporations's DIAGNOdent™ caries detector can be used to provide a diagnostic indication. Alternatively, diagnostic values can be determined using visual inspection and probing. From the diagnostic test, the user obtains a quantitative value 106. The value corresponding to the patient's tooth and region selected is then stored on the device 108 using the numeric keypad of FIG. G to input the quantitative diagnostic value indicated by the probe or derived by visual inspection. Entering the value can be done manually (keyboard, touch pad, voice recognition, and the like) or the dental probe/examination device can be in direct communication with the device. In addition to allowing input of a quantitative value, an alternative embodiment includes icons, such as those depicted in FIGS. 5 and 6, on the display to allow additional descriptive input. Advantageously, a user can employ a caries detection dental probe to both obtain a quantitative diagnostic value and as a stylus for entering information in the invention.

After recording information for the current region, an indication, such as the dot 48 depicted in FIG. H, is provided to notify the user that the region has been examined. Once a value for a region has been recorded, the user selects another region to be examined. In this manner, the user takes measurement and records the values for each region of the selected tooth and proceeds to the next tooth by clicking on the appropriate icons of the screen display until all of a patient's teeth have been examined.

As an additional feature of the invention, once a measurement has been taken, the device then compares the current value against a range of values in step 110. If the value is normal in step 112, then the value is compared to the last recorded value in step 114. If the current value is greater than the last recorded value then caries progression (demineralization) is recorded in step 116 and the dentist proceeds to another site on that same tooth in step 128 returning to step 102 or selects another tooth in step 100. If the current value is equal to the last recorded value in step 118, then no change is recorded for the caries in step 120 and the dentist proceeds to another site on that same tooth in step 128 returning to step 102 or selects another tooth in step 100. If the current value is less than the last recorded value, then caries demineralization is recorded in step 122 and the dentist proceeds to another site on that same tooth in step 128 returning to step 102 or selects another tooth in step 100. On the other hand, if the values in step 112 were not normal, then the value is checked to see if the inner ½ enamel to enamel-dentin junction has been reached in step 124. If not, then decay is in dentin is recorded in step 126. If so, then the process proceeds to step 114 to continue to compare values. In another embodiment, the recorded values are further processed, for example, by using a clinical decision support system. The recorded data is automatically surveyed to provide a recommended course of clinical management of the decay. In conjunction with patient screening history, the values derived from the above process are used to establish risk levels and x-ray intervals as described previously.

The current invention also allows the user to transfer information to other computers, for example, using an interface such as PALM™ Corporation's HOTSYNC™ capability. However, other techniques for communicating with other computing platforms can be used, including, for example: infrared, universal serial bus, RS-232, Ethernet, and RF communication methods. In addition, information transfer may be accomplished by various intermediate memory storage devices, such as memory cards, diskettes, or PCMCIA cards. Using HOTSYNC for example, users can both write information to and read information from another computer. To transfer information, the user installs the PDA in a HOTSYNC cradle, exits the invention's program, and presses the HOTSYNC button provided on the PDA. By performing a HOTSYNC, the patient database is automatically transferred to the host computer. After the information is transferred to another computer, the information can be imported into a word processing program for further editing and, preferably, formatted for entry into standard medical logs. In addition, the information can be used for billing, insurance, and formatted to be provided to a patient to indicate condition of the patients's teeth and recommended prophylactic action. Information such as appointment information, caries databases, new patient information, or new software can also be downloaded from other computers to the PDA. Based on the foregoing specification, the invention may be implemented using computer programming or engineering techniques including computer software, firmware, hardware or any combination or subset thereof. Any such resulting program, having computer-readable code means, may be embodied or provided within one or more computer-readable media, thereby making a computer program product, i.e., an article of manufacture, according to the invention. The computer readable media may be, for instance, a fixed (hard) drive, diskette, optical disk, magnetic tape, semiconductor memory such as read-only memory (ROM), etc., or any transmitting/receiving medium such as the Internet or other communication network or link. The article of manufacture containing the computer code may be made and/or used by executing the code directly from one medium, by copying the code from one medium to another medium, or by transmitting the code over a network.

One skilled in the art of computer science will easily be able to combine the software created as described with appropriate general purpose or special purpose computer hardware to create a computer system or computer subsystem embodying the method of the invention. An apparatus for making, using or selling the invention may be one or more processing systems including, but not limited to, a central processing unit (CPU), memory, storage devices, communication links and devices, servers, I/O devices, or any sub-components of one or more processing systems, including software, firmware, hardware or any combination or subset thereof, which embody the invention. User input may be received from the keyboard, mouse, pen, voice, touch screen, or any other means by which a human can input data into a computer, including through other programs such as application programs and devices.

It should be understood that the examples and embodiments described herein are for illustrative purposes only and that various modifications or changes in light thereof will be suggested to persons skilled in the art and are to be included within the spirit and purview of this application and the scope of the appended claims.

What is claimed is:

1. An interactive system for recording carious lesion information comprising:
    a) a computing device comprising a display, a central processing unit (CPU), operating system software, memory for storing data, a user interface, and input/output capability for reading and writing data;
    b) a patient database comprising patient dental records;
    c) a graphical user interface (GUI) having at least one linked, interactive screen display, said display comprising:
        1) a first display area comprising an anatomically correct diagram of a set of teeth, wherein said teeth represent a patient's teeth according to the corresponding data stored for the patient in said patient information database, said teeth including indicia to indicate condition of a patient's teeth, wherein said teeth are interactive icons, and each of said teeth can be selected to link to a representative diagram of a selected patient's tooth;
        2) a second display area, operatively linked to said first display area, comprising a representative diagram of the coronal morphology of a tooth selected from said teeth, wherein said tooth is an interactive tooth icon divided into selectable regions corresponding to the coronal morphology of said selected tooth, wherein said selectable regions are interactive region icons, each of said region icons having a region identifier to uniquely identify said selectable region;

3) a third display area having operable diagnostic icons, indicative of diagnostic information, wherein said diagnostic icons allow a user to input and record diagnostic information for each said region of said tooth selected and displayed in said second display area; and
4) a fourth display area, associated with said tooth icon displayed in said second display area, comprising a scrollable window to display diagnostic information recorded for the selected patient's tooth, wherein said displayed diagnostic information corresponds to said diagnostic information input using said diagnostic icons in said third display area; and d) computer program code for:
1) providing the capability to allow navigating among elements of said linked, interactive screen display;
2) providing interactive icons to allow entering and editing of said carious lesion information;
3) allowing selection of a patient from said patient database;
4) recording the condition of a selected patient's teeth by:
   i) receiving one of said tooth icons selections from said diagram of a set of teeth;
   ii) displaying said tooth icon;
   iii) receiving one of said region icons selections of said selected tooth icon;
   iv) receiving at least one of said diagnostic icons selections to record the condition of a patient's tooth corresponding to said selected tooth region;
   v) displaying said recorded condition;
   vi) providing the capability to allow verifying and editing of said recorded condition; and
   vii) repeating steps i)-vi) until the condition of each region of each of the selected patient's teeth has been received and recorded;

wherein said computing device executes said computer code and provides said GUI to allow a user to interactively record carious lesion information.

2. The system of claim 1, wherein said computing device is a Personal Digital Assistant (PDA).

3. The system of claim 1, wherein said teeth are human teeth.

4. The system of claim 1, further comprising a system for automatically analyzing said recorded condition for each selected patient's tooth to provide a recommendation for clinical management of each selected patient's tooth.

5. The system of claim 1, further comprising a system for computing and indicating a caries risk level for a dental patient based on said recorded conditions of the patient's teeth and patient screening information maintained in said patient database.

6. The system of claim 5, further comprising a system for computing and indicating a dental x-ray interval for a dental patient based on the patient's said risk level, the patient's age, and the time interval elapsed since the patient's last dental x-ray was taken.

7. The system of claim 1, further comprising a system for graphically capturing an image of the coronal morphology of at least one of a patient's teeth, importing said image into said patient information database, creating an interactive image icon from said image, assigning interactive regions to said image icon corresponding to the morphology of said at least one of the patient's teeth, and providing said image icon on said GUI in said first and second display areas whenever the associated patient's dental records are retrieved.

8. The system of claim 1, further comprising a region insertion tool to manually move and add interactive regions to said tooth icons.

9. The system of claim 1, further comprising a caries detection dental probe to determine the condition of said selected region of a patient's tooth and provide a decay reading value for said selected region.

10. The system of claim 9, further comprising an interactive numeric display on said GUI to allow reporting of said decay reading value by selecting the corresponding value on said numeric display.

11. The system of claim 9, wherein said caries detection dental probe is in communication with said computer system and automatically updates said patient information database for the selected region of a patient's tooth being probed.

12. The system of claim 11, wherein said computer system is remotely located with respect to said caries detection dental probe.

13. The system of claim 1, further comprising a system for characterizing and indicating tooth condition, comprising:
a) a caries database of standard carious lesion conditions; and
b) computer code for automatically comparing said recorded condition to standard carious lesion conditions maintained in said caries database, comparing said recorded tooth condition to a previously stored tooth condition maintained in said patient database, for the same tooth, and recording and providing a characterization indication of present tooth condition based on said comparisons.

14. The system of claim 13, wherein said characterization indication further comprises a first graphical indicator for no difference between a recorded tooth condition value and a corresponding previously recorded tooth condition value and for a recorded tooth condition value less than a corresponding previously recorded tooth condition value, and a second graphical indicator for a recorded tooth condition value more tan a corresponding previously recorded tooth condition value.

15. An interactive system for recording carious lesion information comprising:
a) a computing device comprising a display, a central processing unit (CPU), operating system software, memory for storing data, a user interface, and input/output capability for reading and writing data;
b) a patient database comprising patient dental records;
c) a varies detection dental probe providing decay reading values indicative of tooth condition;
d) a graphical user interface (GUI) having at least one linked, interactive screen display, said display comprising:
   1) a first display area comprising an anatomically correct diagram of a set of teeth, wherein said teeth represent a patient's teeth according to the corresponding data stored for the patient in said patient information database, said teeth including indicia to indicate condition of a patient's teeth, wherein said teeth are interactive icons, and each of said teeth can be selected to link to a representative diagram of a selected patient's tooth;
   2) a second display area, operatively linked to said first display area, comprising a representative diagram of the coronal morphology of a tooth selected from said teeth, wherein said tooth is an interactive tooth icon divided into selectable regions corresponding to the coronal morphology of said selected tooth, wherein said selectable regions are interactive region icons, each of said region icons having a region identifier to uniquely identify said selectable region;

3) a third display area having operable diagnostic icons, indicative of diagnostic information, wherein said diagnostic icons allow a user to input and record diagnostic information for each said region of said tooth selected and displayed in said second display area; and e) computer program code for:
1) providing the capability to allow navigating among elements of said linked, interactive screen display;
2) providing interactive icons to allow entering and editing of said carious lesion information;
3) allowing selection of a patient from said patient database; and
4) recording the condition of a selected patient's teeth by:
   i) receiving one of said tooth icons selections from said diagram of a set of teeth;
   ii) displaying said tooth icon;
   iii) receiving one of said region icons selections of said selected tooth icon;
   iv) receiving at least one of said diagnostic icons selections to record the condition of a patient's tooth corresponding to said selected tooth region;
   v) displaying said recorded condition;
   vi) providing the capability to allow verifying and editing of said recorded condition; and
   vii) repeating steps i)-vi) until the condition of each region of each of the selected patient's teeth has been received and recorded;

wherein said computing device executes said computer code and provides said GUI to allow a user to interactively record carious lesion information using said caries detection dental probe.

16. The system of claim 15, wherein said computing device is a PDA.

17. The system of claim 15, wherein said caries detection dental probe is in communication with said computer system and automatically updates said patient information database for the selected region being probed.

18. The system of claim 17, wherein said computer system is remotely located with respect to said caries detection dental probe.

19. The system of claim 15, further comprising a system for characterizing and indicating tooth condition based on said diagnostic information, comprising:
a) a caries database of standard carious lesion values;
b) computer code for automatically comparing a decay reading value to standard carious lesion values maintained in said caries database, comparing said decay reading value to a previously stored value, maintained in said patient database, for the same tooth, and recording and providing a characterization indication of present tooth condition based on said comparisons.

20. The system of claim 19, wherein said indication further comprises a first graphical indicator for no difference between a decay reading value and a corresponding previously stored decay reading value and for a decay reading less than a corresponding previously stored decay reading value, and a second graphical indicator for a decay reading more than a corresponding previously stored decay reading value.

21. The system of claim 15, flitter comprising a system for computing and indicating a caries risk level for a dental patient based on said recorded conditions of the patient's teeth and patient screening information maintained in said patient database.

22. The system of claim 21, further comprising a system for computing and indicating a dental x-ray interval for a dental patient based on the patient's said risk level, the patient's age, and the time interval elapsed since the patient's last dental x-ray was taken.

23. A method for recording carious lesion information comprising:
a) providing a computing device comprising a display, a central processing unit (CPU), operating system software, memory for storing data, a user interface, and input/output capability for reading and writing data;
b) providing a patient database comprising patient dental records;
c) providing a graphical user interface (GUI) having at least one linked, interactive screen display;
d) selectively displaying an anatomically correct diagram of a set of teeth, wherein said teeth represent a patient's teeth according to the corresponding data stored for the patient in said patient information database, said teeth including indicia to indicate condition of a patient's teeth comprising information on severity, activity (demineralization or remineralization), and/or cavitation state (non-cavitated or cavitated) of the patient's teeth, wherein said teeth are interactive icons, and each of said teeth can be selected to link to a representative diagram of a selected patient's tooth;
e) selectively displaying a representative diagram of the coronal morphology of a tooth selected from said teeth, wherein said tooth is an interactive tooth icon divided into selectable regions corresponding to the coronal morphology of said selected tooth, wherein said selectable regions are interactive region icons, each of said region icons having a region identifier to uniquely identify said selectable region;
f) selectively displaying operable diagnostic icons, indicative of diagnostic information, wherein said diagnostic icons allow a user to input and record diagnostic information for each said region of said tooth selected and displayed;
g) receiving a patient selection and retrieving requested patient data from said patient database; and
h) receiving data to record the condition of a selected patient's teeth by:
   1) receiving one of said tooth icons selections of said diagram of a set of teeth;
   2) displaying said tooth icon;
   3) receiving one of said region icon selections of said selected tooth icon;
   4) receiving at least one of said diagnostic icons selections to record the condition of a patient's tooth corresponding to said selected tooth region; and
   5) repeating steps 1)-4) until the condition of each region of each of the selected patient's teeth has been received and recorded.

24. The method of claim 23, further comprising:
a) providing a fourth display area of said interactive screen display, associated with said interactive tooth icon, comprising a scrollable window to display diagnostic information recorded for the selected patient's tooth, wherein said displayed diagnostic information corresponds to said diagnostic information input using said diagnostic icons;
b) displaying said recorded condition of each selected tooth region of each selected patient's tooth in said fourth display area; c) allowing verifying and editing of said recorded conditions; and d) repeating steps (b) and (c) until the condition of each region of each of the selected patient's teeth has been recorded.

25. The method of claim 23, wherein receiving data further comprises receiving data from a caries detection dental probe.

26. The method of claim 23, further comprising characterizing and indicating the condition of said selected region of the selected patient's tooth by:
   a) providing a caries database of standard carious lesion conditions;
   b) comparing said recorded condition to standard carious lesion conditions maintained in said database to provide a first comparison;
   c) determining, providing, and recording the extent of caries based on said first comparison;
   d) comparing said recorded tooth condition to a previously recorded tooth condition maintained in said patient database for same said selected region of the selected patient's tooth to provide a second comparison;
   e) determining, providing, and recording an indication of present tooth condition based on said second comparison; and
   f) repeating steps (b)-(e) until the condition of each region of each of the selected patient's teeth has been characterized, indicated, and recorded.

27. The method of claim 23, further comprising automatically analyzing the recorded condition for each said selected region of the selected patient's tooth and providing a recommendation for clinical management of each said selected region of the selected patient's tooth.

28. The method of claim 23, further comprising computing and indicating a caries risk level for a dental patient based on said recorded conditions of the patient's teeth and patient screening information maintained in said patient database.

29. The method of claim 28, further comprising a method for computing and indicating a dental x-ray interval for a dental patient based on the patient's said risk level, the patient's age, and the time interval elapsed since the patient's last dental x-ray was taken.

30. The method of claim 23, further comprising receiving a graphically captured image of the coronal morphology of at least one of a patient's teeth, importing said image into said patient information database, creating an interactive image icon from said image, assigning interactive regions to said image icon corresponding to the morphology of said tooth, and providing said image icon on said GUI in said first and second display areas whenever the associated patient's dental records are retrieved.

31. The method of claim 23, further comprising allowing manual movement and addition of interactive regions to said tooth icons.

32. A method for recording carious lesion information comprising:
   a) providing a computing device comprising a display, a central processing unit (CPU), operating system software, memory for storing data, a user interface, and input/output capability for reading and writing data;
   b) providing a patient database comprising patient dental records;
   c) providing a graphical user interface (GUI) having at least one linked, interactive screen display;
   d) selectively displaying an anatomically correct diagram of a set of teeth, wherein said teeth represent a patient's teeth according to the corresponding data stored for the patient in said patient information database, said teeth including indicia to indicate condition of a patient's teeth comprising information on severity, activity (demineralization or remineralization), and/or cavitation state (non-cavitated or cavitated) of the patient's teeth, wherein said teeth are interactive icons, and each of said teeth can be selected to link to a representative diagram of a selected patient's tooth;
   e) selectively displaying a representative diagram of the coronal morphology of a tooth selected from said teeth, wherein said tooth is an interactive tooth icon divided into selectable regions corresponding to the coronal morphology of said selected tooth, wherein said selectable regions are interactive region icons, each of said region icons having a region identifier to uniquely identify said selectable region;
   f) selectively displaying operable diagnostic icons, indicative of diagnostic information, wherein said diagnostic icons allow a user to input and record diagnostic information for each said region of said tooth selected and displayed;
   g) selecting a patient from said patient database; and
   h) recording the condition of a selected patient's teeth by:
      1) selecting one of said tooth icons from said diagram of a set of teeth;
      2) displaying said tooth icon;
      3) selecting one of said region icons of said selected tooth icon;
      4) examining the corresponding region of the selected patient's tooth;
      5) recording the condition of a patient's tooth corresponding to said selected tooth region by selecting the appropriate diagnostic icons displayed; and
      6) repeating steps 1)-5) until the condition of each region of each of the selected patient's teeth has been recorded.

33. The method of claim 32, wherein examining the corresponding region of the selected patient's tooth further comprises using a caries detection dental probe to automatically determine the condition of said selected region of the selected patient's tooth.

34. The method of claim 32 further comprising graphically capturing an image of the coronal morphology of at least one of a patient's teeth, importing said image into said patient information database, creating an interactive image icon from said image, assigning interactive regions to said image icon corresponding to the morphology of said at least one of the patient's teeth, and providing said image icon on said GUI in said first and second display areas whenever the associated patient's dental records are retrieved.

35. The method of claim 32, further comprising manually moving and adding interactive regions to said tooth icons.

36. A computer program product recorded on computer readable media for recording carious lesion information comprising:
   a) computer readable media for providing a patient database comprising patient dental records;
   b) computer readable media for providing a graphical user interface (GUI) having at least one linked, interactive screen display, said screen display comprising;
      1) a first display area comprising an anatomically correct diagram of a set of teeth, wherein said teeth represent a patient's teeth according to the corresponding data stored for the patient in said patient information database, said teeth including indicia to indicate condition of a patient's teeth, wherein said teeth are interactive icons, and each of said teeth can be selected to link to a representative diagram of a selected patient's tooth;
      2) a second display area, operatively linked to said first display area, comprising a representative diagram of the coronal morphology of a tooth selected from said teeth, wherein said tooth is an interactive tooth icon divided into selectable regions corresponding to the coronal morphology of said selected tooth, wherein said selectable regions are interactive region icons, each of said region icons having a region identifier to uniquely identify said selectable region; and 3) a third display area having operable diagnostic icons, indicative of diagnostic information, wherein said diagnostic icons allow a user to input and record diagnostic information for each said region of said tooth selected and displayed in said second display area;

c) computer readable media for providing the capability to allow navigating among elements of said linked, interactive screen display;

d) computer readable media for providing interactive icons to allow entering and editing of said carious lesion information;

e) computer readable media for allowing selection of a patient from said patient database; and f) computer readable media for recording the condition of a selected patient's teeth, wherein recording the condition of a selected patient's teeth is performed by:
1) receiving one of said tooth icons selections from said diagram of a set of teeth;
2) displaying said tooth icon;
3) receiving one of said region icons selections of said selected tooth icon;
4) receiving at least one of said diagnostic icons selections to record the condition of a patient's tooth corresponding to said selected tooth region;
5) displaying said recorded condition;
6) providing the capability to allow verifying and editing of said recorded condition; and
7) repeating steps 1)-6) until the condition of each region of each of the selected patient's teeth has been received and recorded.

37. The computer program product recorded on computer readable media of claim 36, further comprising:
a) computer readable media for providing a fourth display area of said interactive screen display, associated with said tooth icon displayed in said second display area, comprising a scrollable window to display diagnostic information recorded for the selected patient's tooth, wherein said displayed diagnostic information corresponds to said diagnostic information input using said diagnostic icons in said third display area;
b) computer readable media for displaying said recorded condition of each selected tooth region of each selected patient's tooth in said fourth display area;
c) computer readable media far allowing verifying and editing of said recorded conditions; and
d) computer readable media for repeating steps (b) and (c) until the condition of each region of each of the selected patient's teeth has been received and recorded.

38. The system of claim 1, wherein the diagnostic icons comprise icons indicating severity depth of lesion and cavitation state (non-cavitated or cavitated).

39. The system of claim 38, wherein the icons indicating severity depth of lesion comprise:
an icon indicating no visible caries or lesion;
an icon indicating a lesion in outer half of enamel;
an icon indicating a lesion in inner half of enamel;
an icon indicating a lesion in outer third of dentin;
an icon indicating a lesion in middle third of dentin; and
an icon indicating a lesion in inner third of dentin or involving pulp.

40. The system of claim 1, wherein the second display area further comprises a representative diagram of the roots of a tooth selected from said teeth.

41. The system of claim 15, wherein the diagnostic icons comprise icons indicating severity depth of lesion and cavitation state (non-cavitated or cavitated).

42. The system of claim 41, wherein the icons indicating severity depth of lesion comprise:
an icon indicating no visible caries or lesion;
an icon indicating a lesion in outer half of enamel;
an icon indicating a lesion in inner half of enamel;
an icon indicating a lesion in outer third of dentin;
an icon indicating a lesion in middle third of dentin; and
an icon indicating a lesion in inner third of dentin or involving pulp.

43. The system of claim 15, wherein the second display area further comprises a representative diagram of the roots of a tooth selected from said teeth.

44. The method of claim 23, wherein the diagnostic icons comprise icons indicating severity depth of lesion and cavitation state (non-cavitated or cavitated).

45. The method of claim 44, wherein the icons indicating severity depth of lesion comprise:
an icon indicating no visible caries or lesion;
an icon indicating a lesion in outer half of enamel;
an icon indicating a lesion in inner half of enamel;
an icon indicating a lesion in outer third of dentin;
an icon indicating a lesion in middle third of dentin; and
an icon indicating a lesion in inner third of dentin or involving pulp.

46. The method of claim 32, wherein the diagnostic icons comprise icons indicating severity depth of lesion and cavitation state (non-cavitated or cavitated).

47. The method of claim 46, wherein the icons indicating severity depth of lesion comprise:
an icon indicating no visible caries or lesion;
an icon indicating a lesion in outer half of enamel;
an icon indicating a lesion in inner half of enamel;
an icon indicating a lesion in outer third of dentin;
an icon indicating a lesion in middle third of dentin; and
an icon indicating a lesion in inner third of dentin or involving pulp.

48. The computer program product recorded on computer readable media of claim 36, wherein the diagnostic icons comprise icons indicating severity depth of lesion and cavitation state (non-cavitated or cavitated).

49. The computer program product recorded on computer readable media of claim 48, wherein the icons indicating severity depth of lesion comprise:
an icon indicating no visible caries or lesion;
an icon indicating a lesion in outer half of enamel;
an icon indicating a lesion in inner half of enamel;
an icon indicating a lesion in outer third of dentin;
an icon indicating a lesion in middle third of dentin; and
an icon indicating a lesion in inner third of dentin or involving pulp.

50. The computer program product recorded on computer readable media of claim 36, wherein the second display area further comprises a representative diagram of the roots of a tooth selected from said teeth.

* * * * *

UNITED STATES PATENT AND TRADEMARK OFFICE
CERTIFICATE OF CORRECTION

| | |
|---|---|
| PATENT NO. | : 7,343,305 B2 |
| APPLICATION NO. | : 10/136903 |
| DATED | : March 11, 2008 |
| INVENTOR(S) | : Benn et al. |

It is certified that error appears in the above-identified patent and that said Letters Patent is hereby corrected as shown below:

Column 3,
Lines 49-50, "to provide linked interactive display screen" should read
--to provide a linked interactive display screen--.
Line 62, "oftooth condition" should read --of tooth condition--.

Column 4,
Line 15, "decision can be automatically suggested" should read
--decisions can be automatically suggested--.

Column 6,
Line 18, "are shown the" should read --are shown in the--.

Column 8,
Line 39, "input into the system in according to" should read
--input into the system according to--.

Column 10,
Line 26, "provides and indication" should read --provides an indication--.
Line 31, "FIG. E" should read --FIG. 10E--.
Line 47, "FIG. G" should read --FIG. 10G--.
Line 58, "FIG. G" should read --FIG. 10G--.

Figure 10H:
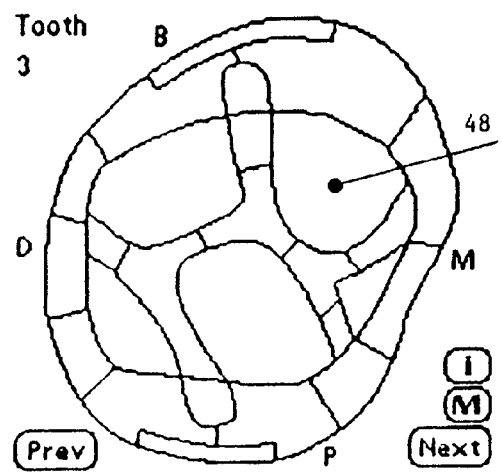
FIG. 10H shows an exemplary screen display for an individual tooth icon having selectable tooth regions, further having an icon to indicate that a region has been examined.

Column 11,
Line 4, "FIG. H" should read --FIG. 10H--.
Line 8, "takes measurement" should read --takes measurements--.

UNITED STATES PATENT AND TRADEMARK OFFICE
CERTIFICATE OF CORRECTION

PATENT NO. : 7,343,305 B2
APPLICATION NO. : 10/136903
DATED : March 11, 2008
INVENTOR(S) : Benn et al.

It is certified that error appears in the above-identified patent and that said Letters Patent is hereby corrected as shown below:

Column 15,
Line 63, "flitter comprising" should read --further comprising--.

Signed and Sealed this

Thirtieth Day of September, 2008

JON W. DUDAS
*Director of the United States Patent and Trademark Office*